United States Patent
Grote et al.

(10) Patent No.: US 9,522,758 B2
(45) Date of Patent: Dec. 20, 2016

(54) BEVERAGE BOTTLING PLANT HAVING AN APPARATUS FOR INSPECTING BOTTLES OR SIMILAR CONTAINERS WITH AN OPTOELECTRIC DETECTION SYSTEM AND AN OPTOELECTRIC DETECTION SYSTEM

(75) Inventors: Frank Joachim Grote, Darmstadt (DE); Carsten Buchwald, Bad Breisig (DE)

(73) Assignee: KHS GmbH, Dortmund (DE)

( * ) Notice: Subject to any disclaimer, the term of this patent is extended or adjusted under 35 U.S.C. 154(b) by 803 days.

(21) Appl. No.: 12/626,922

(22) Filed: Nov. 29, 2009

(65) Prior Publication Data

US 2010/0141756 A1 Jun. 10, 2010

Related U.S. Application Data

(63) Continuation-in-part of application No. PCT/EP2008/004212, filed on May 28, 2008.

(30) Foreign Application Priority Data

May 31, 2007 (DE) .................. 10 2007 025 524

(51) Int. Cl.
| | |
|---|---|
| *H04N 7/18* | (2006.01) |
| *B65C 9/06* | (2006.01) |
| *G01B 11/04* | (2006.01) |
| *G01B 11/24* | (2006.01) |
| *G01B 11/245* | (2006.01) |
| *G01N 21/90* | (2006.01) |

(52) U.S. Cl.
CPC ............. *B65C 9/067* (2013.01); *G01B 11/04* (2013.01); *G01B 11/24* (2013.01); *G01B 11/245* (2013.01); *G01N 21/9045* (2013.01)

(58) Field of Classification Search
None
See application file for complete search history.

(56) References Cited

U.S. PATENT DOCUMENTS

| | | | |
|---|---|---|---|
| 4,509,081 A | | 4/1985 | Peyton et al. |
| 4,584,469 A | | 4/1986 | Lovalenti |
| 5,020,908 A | | 6/1991 | Hermann |
| 5,136,157 A | * | 8/1992 | Apter et al. .............. 250/223 B |
| 5,405,015 A | | 4/1995 | Bhatia et al. |
| 5,515,159 A | * | 5/1996 | Sites et al. ................ 356/237.1 |

(Continued)

FOREIGN PATENT DOCUMENTS

| | | |
|---|---|---|
| DE | 101 40 010 A1 | 3/2003 |
| DE | 102 57 749 A1 | 7/2004 |

(Continued)

*Primary Examiner* — John B Walsh
(74) *Attorney, Agent, or Firm* — Nils H. Ljungman & Associates

(57) ABSTRACT

An optoelectric detection system and method for detecting surface features on containers is disclosed herein. The system has an electronic camera arrangement and an illuminating arrangement configured to illuminate surfaces of containers. The illuminating arrangement comprises a strip-shaped light source that extends in the direction of movement of containers. The electronic camera arrangement and illuminating arrangement are adjustable relative to one another and configured to provide different angles of incidence of light on surfaces of containers and/or different angles of images of light reflected from surfaces of containers.

20 Claims, 9 Drawing Sheets

(56) References Cited

U.S. PATENT DOCUMENTS

| | | | |
|---|---|---|---|
| 5,729,340 A | 3/1998 | Griesbeck et al. | |
| 6,172,355 B1 | 1/2001 | Gast et al. | |
| 7,342,655 B2 * | 3/2008 | Yagita | G01N 21/9027 250/223 B |
| 2005/0248766 A1 | 11/2005 | Niedermeier et al. | |

FOREIGN PATENT DOCUMENTS

| | | |
|---|---|---|
| DE | 10 2005 023 534 A1 | 11/2006 |
| EP | 0 222 959 A | 5/1987 |
| EP | 1 617 208 A1 | 1/2006 |
| WO | WO 01/55705 A | 8/2001 |

\* cited by examiner

BEVERAGE BOTTLING PLANT HAVING AN APPARATUS FOR INSPECTING BOTTLES OR SIMILAR CONTAINERS WITH AN OPTOELECTRIC DETECTION SYSTEM AND AN OPTOELECTRIC DETECTION SYSTEM

CONTINUING APPLICATION DATA

This application is a Continuation-In-Part application of International Patent Application No. PCT/EP2008/004212, filed on May 28, 2009, which claims priority from Federal Republic of Germany Patent Application No. 10 2007 025 524.3, filed on May 31, 2007. International Patent Application No. PCT/EP2008/004212 was pending as of the filing date of this application. The United States was an elected state in International Patent Application No. PCT/EP2008/004212.

BACKGROUND

1. Technical Field

The present application relates to a beverage bottling plant having an apparatus for inspecting bottles or similar containers with an optoelectric detection system and an optoelectric detection system.

2. Background Information

Background information is for informational purposes only and does not necessarily admit that subsequently mentioned information and publications are prior art.

In container processing machines, for example in labelling machines, optoelectric detection systems are known for detecting profile features and/or shape features on containers, especially also for aligning containers with respect to said features whenever labels or other products are to be applied to the containers within a predetermined spatial reference relative to the profile features and/or shape features.

These types of optoelectric detection systems, as a rule, are made up by at least one electronic camera for detecting or imaging the respective profile feature and/or shape feature and one associated illuminating device. In a computer-controlled image processing system, for example, the image data supplied by the camera is then evaluated, for example for aligning the containers by rotating or pivoting them about their container axis. If containers of different shapes or with different profile features and/or shape features are processed in one and the same system, a clear evaluation of the image data supplied by the at least one camera is often not possible or is or may only be possible in a very limited manner.

OBJECT OR OBJECTS

An object of at least one possible embodiment of the present application is to provide a detection system that avoids or substantially avoids these disadvantages.

SUMMARY

At least one possible embodiment of the present application teaches an optoelectric detection system for detecting profile features and/or shape features of bottles or similar containers that are moving on a conveyor in a direction of conveyance, in which the optoelectric detection system has at least one camera arrangement that includes at least one electronic camera and at least one associated illuminating device for illuminating the containers at least in the region of their profile features and/or shape features that are to be detected by the detection system, wherein the at least one illuminating device is in the form of a strip-shaped light source that extends in the direction of movement of the containers, and in that the illuminating device and/or the at least one camera are adjustable relative to each other for different angles of incidence of the light and/or for different angles of image recording.

Further developments, advantages and application possibilities of at least one possible embodiment of the present application are also produced from the subsequent description of exemplary embodiments and from the Figures. In principle, in this case, all described and/or graphically represented features are objects of at least one possible embodiment of the present application, individually or in arbitrary combination, irrespective of their summarization in the claims or their dependency.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

At least one possible embodiment of the present application is described below by way of the Figures, in which, in detail.

DESCRIPTION OF EMBODIMENT OR EMBODIMENTS

Figure 1:
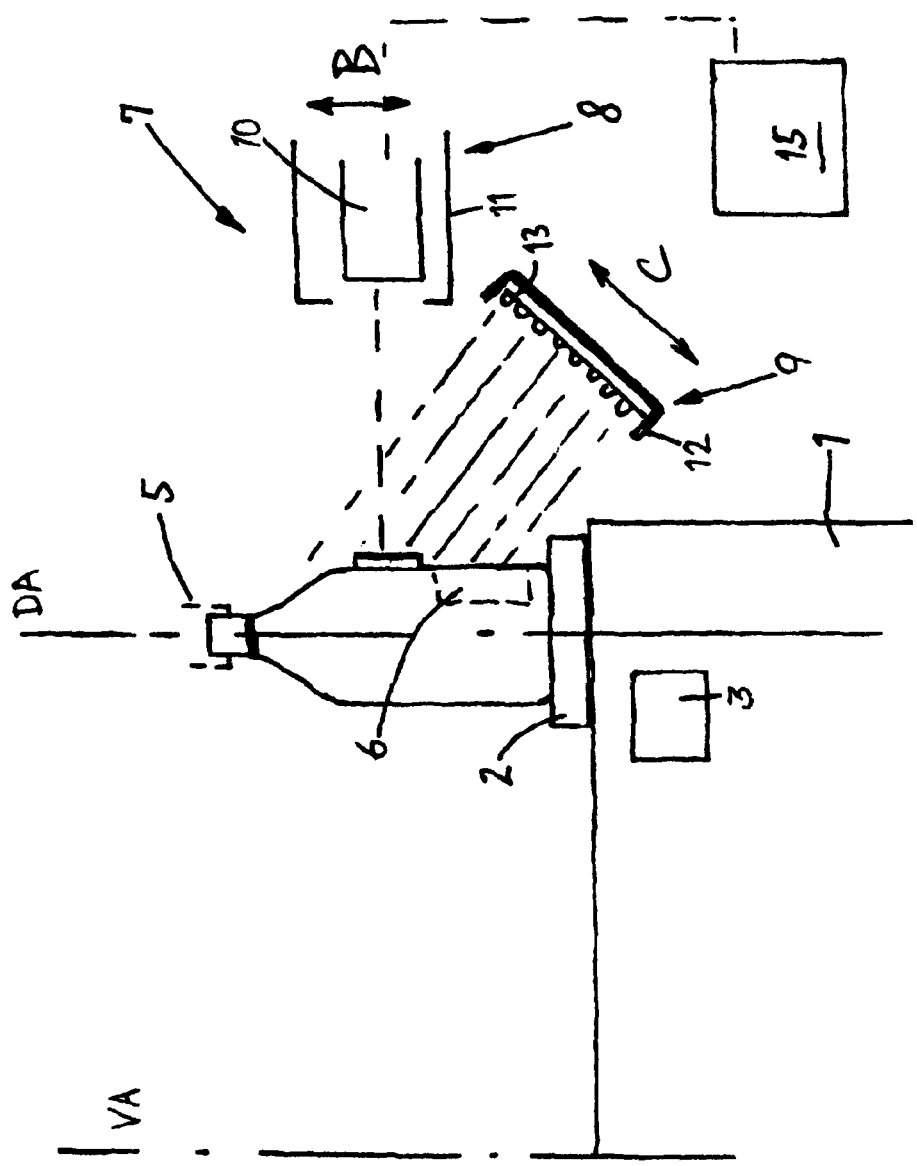
FIG. 1 is a schematic partial representation of a vertical section through a turntable, with a bottle positioned on a rotary disc and with an optoelectric detection system positioned to the side of the turntable for detecting profile features and/or shape features of the bottles that are moving past on the turntable.

In the Figures the reference 1 is given to a turntable of a bottle or container processing machine, for example a labeling machine, said turntable being rotatably driveable about a vertical machine axis VA in a direction of rotation A. At the periphery of the turntable 1, distributed about the axis VA, are a plurality of container supports in the form of rotary discs 2, which are each individually rotatable or pivotable in a controlled manner about a vertical rotary disc axis DA by means of a rotary drive or setting drive 3. For the processing, for example for the labeling, on each rotary disc 2 there is a bottle 4 standing on its bottle bottom positioned with the bottle axis equi-axially or substantially equi-axially to the axis DA. Rams 5 keep the bottles 4 on the respective rotary disc 2 safe from falling over.

The bottles 4 are provided on their outer surface with a noticeable profile feature and/or shape feature 4.1. The respective profile feature and/or shape feature 4.1 can be of the most varied kind, for example it can be in the form of a three-dimensional raised profile feature or shape feature or a recessed, three-dimensional profile feature or shape feature on the outer surface of the bottles 4, it can also, for example, be in the form of seals, embossings, decorations etc. In addition, the profile feature and/or shape feature can also be two-dimensional.

For example for applying labels 6 in a predetermined spatial allocation relative to the respective profile feature and/or shape feature 4.1, it is necessary or desirable to rotate the bottle 4, positioned on the associated rotary disc 2, about the axis DA in a controlled manner by means of appropriate activation of the respective drive 3, such that, with respect to its profile feature and/or shape feature 4.1, it has a predetermined orientation before it is moved past a labeling unit (not shown) of the processing machine by the turntable 1.

The individual bottles 4 are supplied to the processing machine or the rotary discs 2 by means of a conveyor and a bottle inlet, standing upright in an arbitrary orientation with respect to the profile feature and/or shape feature 4.1. In order to detect said arbitrary orientation (actual value) and to control the rotary movement of the respective rotary disc 2 about the axis DA necessary or desired for the required or desired orientation, an optoelectric detection system 7 is provided on a part of the processing machine that is not rotating with the turntable 1, said optoelectric detection system having, among other things, a camera arrangement 8 and an illuminating device 9. The detection system 7, in the specific embodiment represented, is positioned on the side of the circular path of movement of the rotary disc 1 remote from the axis VA, i.e. radially outside said path of movement.

The camera arrangement 8, in the specific embodiment represented, comprises a total of four electronic cameras 10, which are positioned in a common housing 11 in such a manner that the bottles 4 standing on the rotary discs 2 of the turntable 1 are always or virtually always visually recorded by each camera 10 in the region of their profile feature and/or shape feature. As the double arrow B in FIG. 1 indicates, the individual cameras 10 are provided so as to be adjustable on an individual basis, for example, but the housing 11 as a whole is also adjustable so as to adjust the height in the vertical axis, to adjust the spacing between camera arrangement 8 and turntable 1 in a horizontal axis, to pivot the camera arrangement 8 about a horizontal axis parallel or substantially parallel to an imaginary tangent onto the turntable 1 or circular path of the rotary disc 2 and to pivot about a vertical axis.

In addition, the cameras 10 are positioned in the housing 11 such that each camera 10 is at the same spacing from the path of movement along which the rotary discs 2 or their axes DA are moving.

The illuminating device 9 is in the form of a curved light strip, which faces the turntable 1 with its concave side, surrounds said turntable on part of its periphery at a spacing and extends in the direction of rotation A, and comprises, among other things, a correspondingly curved, tub-like housing 12, in which a plurality of electrically operated elements 13 that emit light are provided in the form of LEDs.

The LED arrangement formed by the LEDs 13 is, for example, segmented, i.e. it is produced, among other things, by a plurality of LED segments 14, which follow one after another in the longitudinal direction of the housing 12 and, in this case for instance, in the direction of rotation A of the turntable 1, each one of which, in its turn, being produced by an arrangement with a plurality of LEDs 13. In the case of the specific embodiment represented, the illuminating device 9 extends over an angular region of the rotational movement of the turntable 1, which (angular region) is greater than the angular region captured by the camera arrangement 8, such that an optimum level of illumination of the bottles 4 passing by is ensured or virtually ensured by the illuminating device 9 even for the first and last camera 10 of the camera arrangement 8, with respect to the direction of rotation A of the turntable 1. The illuminating device 9, in addition, is adjustable and pivotable, in at least one possible embodiment also about at least one horizontal axis parallel or substantially parallel to an imaginary tangent to the circular path of movement of the rotary disc 2 or its axis DA, as is indicated by the double arrow C in FIG. 1. This means that, in an optional manner, illumination of the bottles 4 or of their profile features and/or shape features 4.1 is possible inclinedly from below or also inclinedly from above in each case at different angles and from the side. As the camera arrangement 8 is also adjustable, the detection system has the following adjustment possibilities:

The camera arrangement 8 or the cameras 10 are aligned with their optical axis or with the axis of the image recording horizontally or substantially horizontally and consequently radially or substantially radially relative to the axis VA onto the profile feature and/or shape feature 4.1, the illuminating device 9 is aligned for illumination of the profile features and/or shape features 4.1 inclinedly from below or inclinedly from above.

The illuminating device 9 is aligned for lateral or, with respect to the axis VA, radial or substantially radial illumination of the profile features and/or shape features, the camera arrangement 8 is aligned for a recording or imaging of the profile features and/or shape features inclinedly from below or inclinedly from above, i.e. the camera arrangement 8 or the cameras 10 are situated below or above the illuminating device and are orientated with their axes inclinedly upwards or inclinedly downwards.

Therefore, by adjusting the camera arrangement 8 or the optical axis of the cameras 10, the angle of the image recording is changed. By adjusting the illuminating device 9, the angle at which the reflected light contacts the bottles 4, is changed. The camera arrangement 8 and the illuminating device 9 are situated on a common side of the path of movement of the bottles 4. The illuminating of the bottles 4 or of their profile features and/or shape features 4.1 is effected consequently by reflected light in the case of this specific embodiment.

Figure 2:
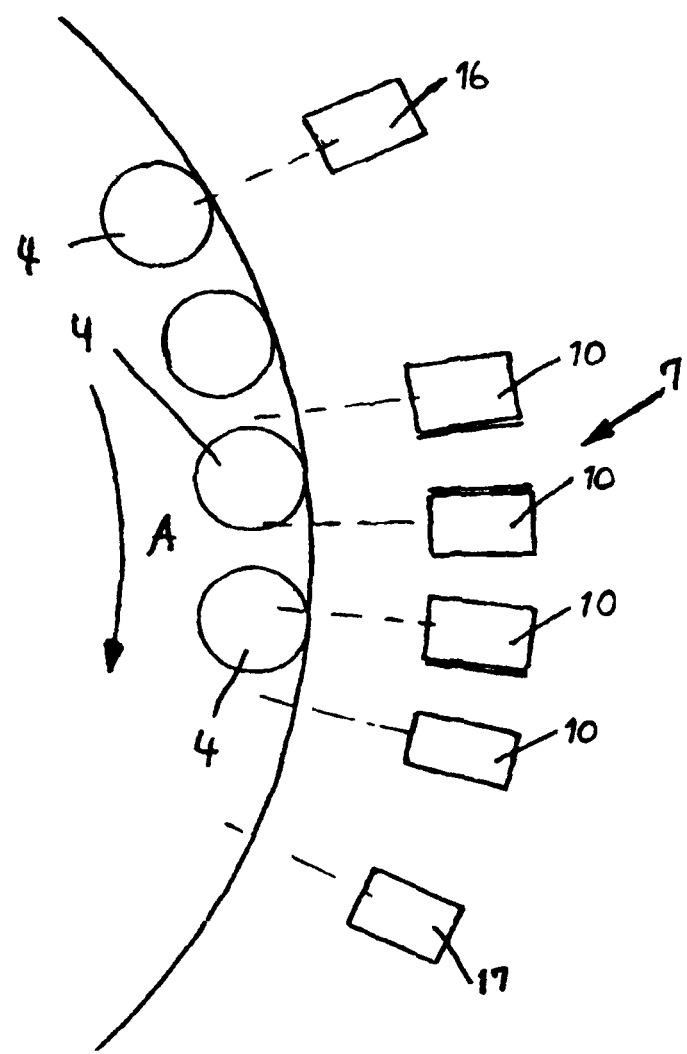
FIG. 2 is a simplified partial representation of a top view of the turntable and of a camera arrangement of the optoelectric system in FIG. 1.

In dependence on the respective embodiment of the profile features or shape features, the optoelectric detection system 7 can be adjusted such that in at least one possible embodiment of the present application a clear, distinctive image of the respective profile feature and/or shape feature 4.1 is generated for evaluation in an image processing system 15. The image data supplied by the camera arrangement is compared to stored image data in said image processing system for activating the respective setting drive 3 in such a manner that the bottle 4 standing on the respective rotary disc 2 finally has the predetermined orientation with respect to its profile feature and/or shape feature 4.1 corresponding to FIG. 2 in such a manner that the respective bottle 4 is then orientated with its profile feature and/or shape feature 4.1 in the direction of rotation A of the turntable 1.

The references 16 and 17 are given to additional cameras that are provided to the side of the turntable 1 on a part of the processing machine that is not entrained with said turntable and by means of which the bottles moving past are recorded. The cameras 16 and 17 then serve for control purposes, thus, for example, the camera 16 upstream of the detection system 7 in the direction of rotation A is used for ascertaining or checking the presence of a bottle 4 on the respective rotary disc 2 and the camera 17 downstream of the detection system 7 is used for ascertaining or checking the precise or substantially precise alignment of the bottles 4.

An advantage of the curved embodiment of the illuminating device 9 is that the spacing between the illuminating device 9 and the bottles 4 in the entire detection region of the optoelectric detection system 7 is constant or substantially constant.

By using several cameras 10, it is also possible to align the bottles 4 even in a high output processing machine, i.e. with the turntable 1 at high speed. The image data supplied by the cameras 10 is then used, for example, such that a provisional alignment of the respective bottle 4 is effected, with the respective rotary disc 2 continually or substantially continually rotating, by using the first or second camera 10 in the direction of rotation A, for example in such a manner that the bottles 4 finally face radially outwards with their profile features and/or shape features 4.1 with respect to the axis VA, a rotating of the rotary disc 2 by 90° then being effected between the next to last and the last camera 10 in the direction of rotation A such that each bottle 4 is oriented with its profile feature and/or shape feature 4.1 in the direction of rotation A.

Figure 1A:
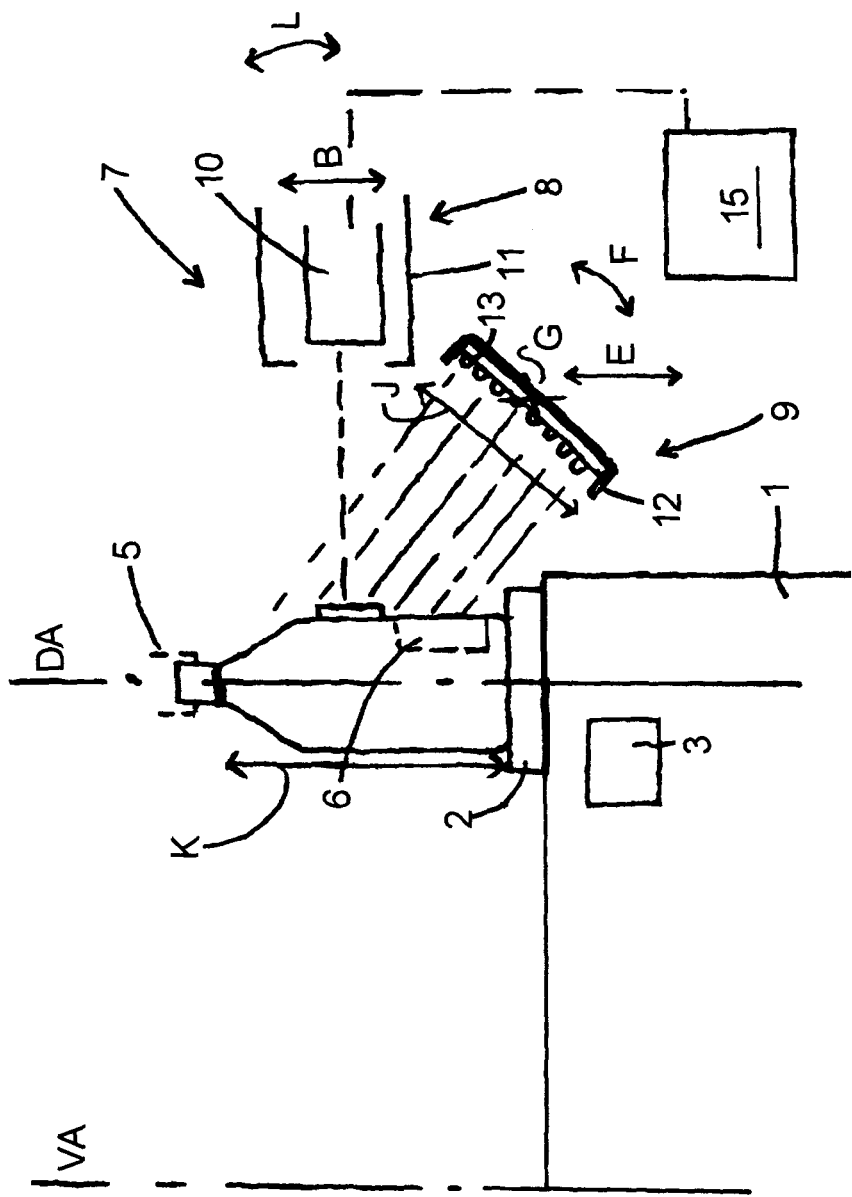
FIG. 1A is the schematic partial representation of a vertical section through a turntable of FIG. 1 showing adjustments to the optoelectric system.
Figure 1B:
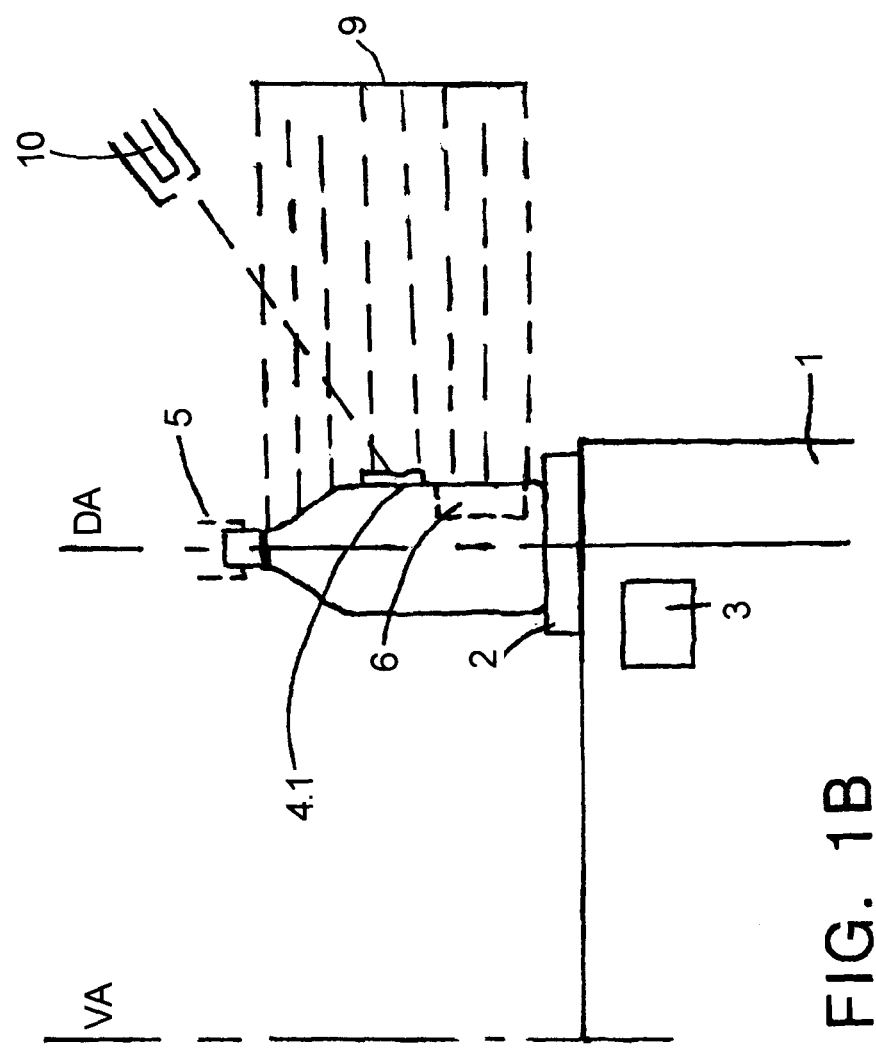
FIG. 1B is the schematic partial representation of a vertical section through a turntable of FIG. 1 showing adjustments to the optoelectric system.

In at least one possible embodiment, illuminating device 9 is in strip form having a length around the axis of rotation, VA, of rotor 1, substantially greater than a width, perpendicular to its length. In at least embodiment of the present disclosure, illuminating device 9 has a width J similar to a height K, of a container 4, as shown in FIG. 1A.

In at least one possible embodiment, housing 12 is substantially cylindrical and houses a plurality LED segments 14 to form a substantially cylindrical illuminating device 9. LED segments 14 may be flat or rectangular. In at least one other possible embodiment, LED segments 14 are cylindrical.

Figure 1C:
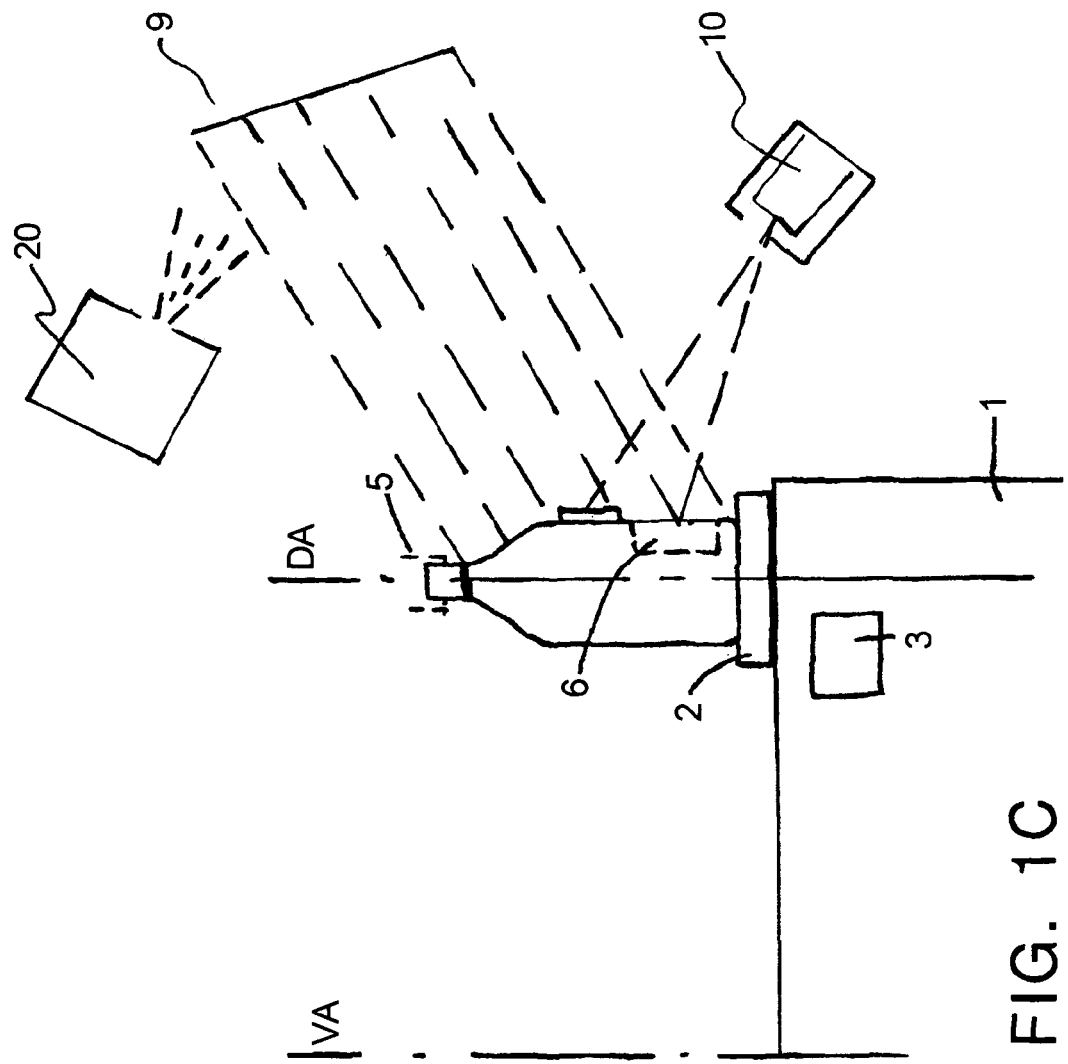
FIG. 1C is the schematic partial representation of a vertical section through a turntable of FIG. 1 showing adjustments to the optoelectric system.

In at least embodiment, illuminating device 9 has a reflective surface and a light source 20, shown in FIG. 1C. Light source 20 and illuminating device 9 are configured and disposed to illuminate at least one profile feature or shape feature on container 4.

In at least one other possible embodiment, housing 12 is substantially in the configuration of a frustum wherein the frustum has a portion of an outer surface of a cone which lies between two parallel planes cutting it, forming an illuminating device 9 in a substantially frustum configuration. In at least one more possible embodiment, each LED segment 14 is substantially trapezoidal, forming an illuminating device 9 in a substantially frustum configuration. In at least one further possible embodiment, each LED segment 14 is substantially a frustum, forming an illuminating device 9 in a substantially frustum configuration.

In at least one possible embodiment, illuminating device 9 has a focal point substantially on the axis of rotation, VA, of turntable or rotor 1. In at least one other possible embodiment, illuminating device 9 has a focal point substantially on the axis of rotation, DA, of rotary disc 2.

Figure 3:
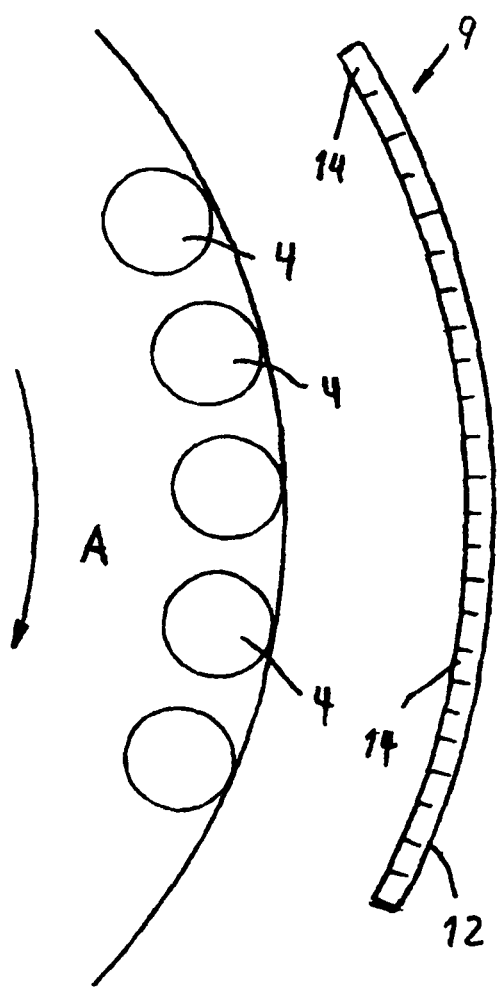
FIG. 3 is a representation as in FIG. 2 of the turntable, together with the illuminating device of the optoelectric detection system in FIG. 1.
Figure 3A:
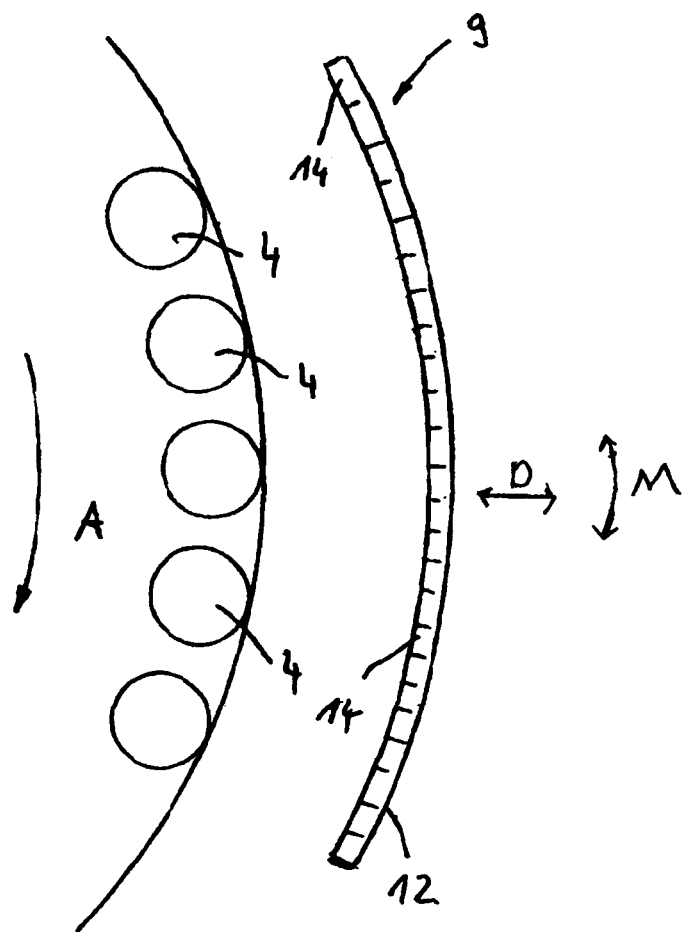
FIG. 3A is a representation as in FIG. 3 showing adjustments to the optoelectric system.

In at least one possible embodiment, illuminating device 9 is movable in a horizontal direction with respect to the axis of rotation, VA, of turntable or rotor 1, as shown as adjustment line D in FIG. 3A. In at least one other possible embodiment, illuminating device 9 is movable in a vertical direction with respect to the axis of rotation, VA, of turntable or rotor 1, as shown as adjustment line E in FIG. 1A. In at least one other possible embodiment, illuminating device 9 is rotatable about a focal point of illuminating device 9 on the axis of rotation, VA, of turntable or rotor 1, or about a focal point of illuminating device 9 on the axis of rotation, DA, of rotary disc 2, as shown as adjustment line F in FIG. 1A. In at least one further possible embodiment, illuminating device 9 is rotatable about a centerline G, of illuminating device 9, as shown centerline G in FIG. 1A. Rotating illuminating device 9, about centerline G, directs the light emitted from illuminating device 9 to sweep a vertical portion of container 4. In at least one further possible embodiment, illuminating device 9 is longitudinally rotatable about the axis of rotation, VA, of rotor 1, as shown adjustment line M in FIG. 3A.

In at least one possible embodiment, illuminating device 9 is movable in a horizontal and vertical direction, as shown by adjustment lines D and E, with respect to the axis of rotation, VA, of rotor 1. In at least one other possible embodiment, illuminating device 9 is movable in a horizontal and vertical direction with respect to the axis of rotation, VA, of rotor 1, as shown as adjustment line C in FIG. 1. In at least one embodiment, illuminating device 9 is configured to adjust its shape upon moving, keeping a focal point in a substantially consistent position. For example, a radius of a frustum shaped illuminating device 9 may increase as illuminating device is moved upwardly along adjustment line C. In at least one embodiment, the frustum shape of illuminating device 9 is adjusted such that its shape changes as if it were sliding up a vertical cone having its sidewall along adjustment line C.

Figure 2A:
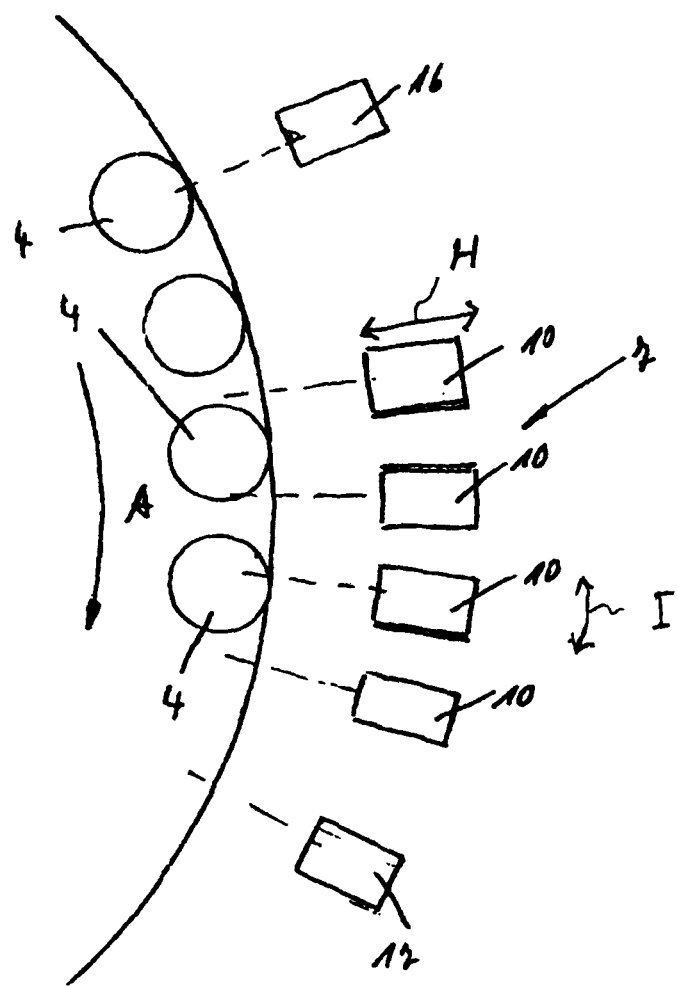
FIG. 2A is a simplified partial representation of a top view of the turntable and of a camera arrangement of the optoelectric system in FIG. 2 showing adjustments to the optoelectric system.

In at least one embodiment, each at least one camera 10 is moveable toward and away from the axis of rotation, VA, of rotor 1, as shown with adjustment line H in FIG. 2A. In at least one other embodiment, each at least one camera 10 is movable around a radius of the axis of rotation, VA, of rotor 1, or around a radius of the axis of rotation, DA, of rotary disc 2, as shown with adjustment line I in FIG. 2A. In at least one additional embodiment, each at least one camera 10 is vertically movable as indicated with adjustment line B in FIG. 1A. In at least one additional embodiment, each at least one camera 10 is rotatable, as shown adjustment line L in FIG. 1A. Rotating each at least one camera 10, as shown adjustment line L in FIG. 1A, directs each at least one camera 10 to sweep and image a vertical portion of container 4 and/or adjust the angle at which an image of container 4 is taken.

In at least one possible embodiment of the instant disclosure, cameras 10 and/or illuminating device 9 are adjustable with respect to one another to change the angle between cameras 10 and illuminating device 9. In at least another possible embodiment, the angle between cameras 10 and illuminating device 9 is adjusted to detect features on the surface of containers 4, such features may include labels, banderoles, defects, cracks, bubbles, foils, foils wrapped around a top neck of a bottle or other container, enamel labels, plastic seals, wax seals, or other seals, and profile features such as outlying features, for example, In one possible embodiment, cameras 10 and/or illuminating device 9 are adjustable during the rotation of rotor 1 and/or rotary disc 2. In another possible embodiment, cameras 10 and/or illuminating device 9 are adjustable during a pause in the rotation of rotor 1 and/or rotary disc 2. In a further possible embodiment, cameras 10 and/or illuminating device 9 are mechanically adjustable. In yet another possible embodiment, cameras 10 and/or illuminating device 9 are electronically or optically adjustable.

Figure 4:
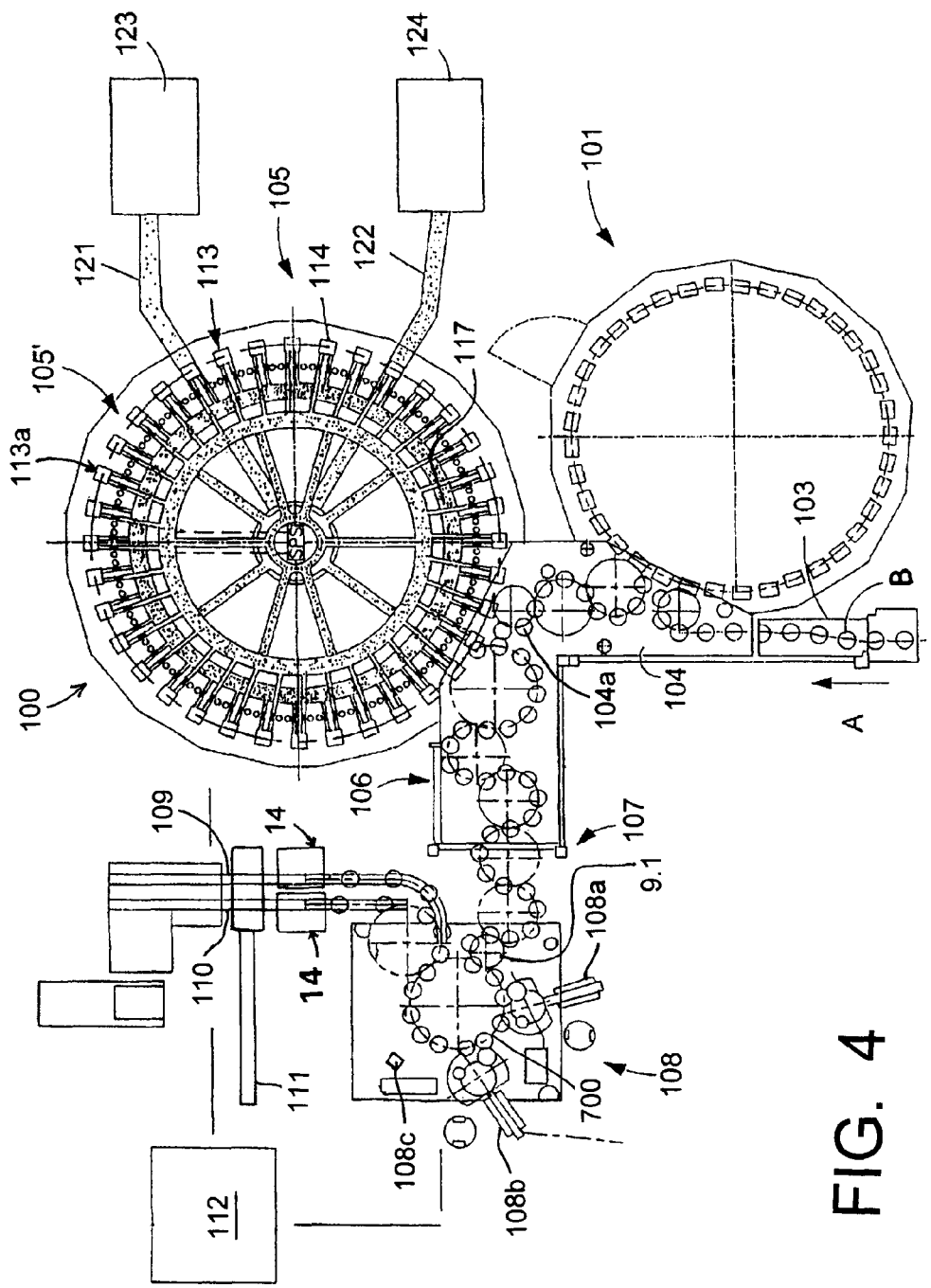
FIG. 4 is a schematic illustration of a container filling plant in accordance with one possible embodiment.

FIG. 4 shows schematically the main components of one possible embodiment example of a system for filling containers, specifically, a beverage bottling plant for filling bottles B with at least one liquid beverage, in accordance with at least one possible embodiment, in which system or plant could possibly be utilized at least one aspect, or several aspects, of the embodiments disclosed herein.

FIG. 4 shows a rinsing arrangement or rinsing station 101, to which the containers, namely bottles B, are fed in the direction of travel as indicated by the arrow A1, by a first conveyer arrangement 103, which can be a linear conveyor or a combination of a linear conveyor and a starwheel. Downstream of the rinsing arrangement or rinsing station 101, in the direction of travel as indicated by the arrow A1, the rinsed bottles B are transported to a beverage filling machine 105 by a second conveyer arrangement 104 that is formed, for example, by one or more starwheels that introduce bottles B into the beverage filling machine 105.

The beverage filling machine 105 shown is of a revolving or rotary design, with a rotor 105', which revolves around a central, vertical machine axis. The rotor 105' is designed to receive and hold the bottles B for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles B to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 4, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle B, the first product or the second product can be filled by means of an appropriate control of the filling product or fluid valves.

Downstream of the beverage filling machine 105, in the direction of travel of the bottles B, there can be a beverage bottle closing arrangement or closing station 106 which closes or caps the bottles B. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles B. In the embodiment shown, the labeling arrangement 108 has three output conveyer arrangement: a first output conveyer arrangement 109, a second output conveyer arrangement 110, and a third output conveyer arrangement 111, all of which convey filled, closed, and labeled bottles B to a bottle inspecting apparatus 20.

The first output conveyer arrangement 109, in the embodiment shown, is designed to convey bottles B that are filled with a first type of liquid beverage supplied by, for example, the supply reservoir 123. The second output conveyer arrangement 110, in the embodiment shown, is designed to convey bottles B that are filled with a second type of liquid beverage supplied by, for example, the supply reservoir 124. The third output conveyer arrangement 111, in the embodiment shown, is designed to convey incorrectly labeled bottles B. To further explain, the labeling arrangement 108 can comprise at least one beverage bottle inspection or monitoring device that inspects or monitors the location of labels on the bottles B to determine if the labels have been correctly placed or aligned on the bottles B. The third output conveyer arrangement 111 removes any bottles B which have been incorrectly labeled as determined by the inspecting device or devices 14.

The beverage bottling plant can be controlled by a central control arrangement 112, which could be, for example, computerized control system that monitors and controls the operation of the various stations and mechanisms of the beverage bottling plant.

The first output conveyer arrangement 109, in the embodiment shown, is designed to convey bottles B that are filled with a first type of liquid beverage supplied by, for example, the supply reservoir 123. The second output conveyer arrangement 110, in the embodiment shown, is designed to convey bottles B that are filled with a second type of liquid beverage supplied by, for example, the supply reservoir 124. The third output conveyer arrangement 111, in the embodiment shown, is designed to convey incorrectly labeled bottles B. To further explain, the labeling arrangement 108 can comprise at least one beverage bottle inspection or monitoring device that inspects or monitors the location of labels on the bottles B to determine if the labels have been correctly placed or aligned on the bottles B. The third output conveyer arrangement 111 removes any bottles B which have been incorrectly labeled as determined by the inspecting device or devices 14.

The beverage bottling plant can be controlled by a central control arrangement 112, which could be, for example, computerized control system that monitors and controls the operation of the various stations and mechanisms of the beverage bottling plant.

At least one possible embodiment of the present application has been described above by way of one exemplary embodiment. It is obvious that numerous changes and variations are possible without departing from the inventive concept underlying at least one possible embodiment of the present application.

At least one possible embodiment relates to an optoelectric detection system for detecting profile features and/or shape features of bottles or similar containers that are moving on a conveyor in a direction of conveyance and rotating about their axis on rotary disc 2.

Optoelectric detection system for detecting profile features and/or shape features of bottles or similar containers that are moving on a conveyor in a direction of conveyance, said optoelectric detection system having at least one camera arrangement that includes at least one electronic camera and at least one associated illuminating device for illuminating the containers at least in the region of their profile features and/or shape features that are to be detected by the detection system.

One feature or aspect of an embodiment is believed at the time of the filing of this patent application to possibly reside broadly in a optoelectric detection system for detecting profile features and/or shape features 4.1 of bottles or similar containers 4 that are moving on a conveyor 10 in a direction of conveyance A, said optoelectric detection system having at least one camera arrangement 8 that includes at least one electronic camera 10 and at least one associated illuminating device 9 for illuminating the containers 4 at least in the region of their profile features and/or shape features 4.1 that are to be detected by the detection system, characterized in that the at least one illuminating device 9 is in the form of a strip-shaped light source that extends in the direction of movement of the containers 4, and in that the illuminating device 9 and/or the at least one camera 10 are adjustable relative to each other for different angles of incidence of the light and/or for different angles of image recording.

Another feature or aspect of an embodiment is believed at the time of the filing of this patent application to possibly reside broadly in the detection system, wherein the at least one illuminating device 9 is realized for illumination with reflected light.

Yet another feature or aspect of an embodiment is believed at the time of the filing of this patent application to possibly reside broadly in the detection system, wherein the at least one camera arrangement 8 and the at least one associated illuminating device 9 are provided on a common side of the path of movement of the containers 4.

Still another feature or aspect of an embodiment is believed at the time of the filing of this patent application to possibly reside broadly in the detection system, wherein the at least one illuminating device 9 is adjustable between a position below the camera arrangement 8 and a position above the camera arrangement 8.

A further feature or aspect of an embodiment is believed at the time of the filing of this patent application to possibly reside broadly in the detection system, wherein the at least one camera arrangement 8 is adjustable between a position below the illuminating device 9 and a position above the illuminating device 9.

Another feature or aspect of an embodiment is believed at the time of the filing of this patent application to possibly reside broadly in the detection system, wherein the at least one camera arrangement 8 and/or the at least one illuminating device 9 are adjustable between a position below a path of movement along which the profile features and/or shape features 4.1 of the containers 4 are moving, and a position above said path of movement.

Yet another feature or aspect of an embodiment is believed at the time of the filing of this patent application to possibly reside broadly in the detection system, wherein the conveyor is a turntable 1 that is rotatably driveable about a vertical machine axis VA, and in that the illuminating device 4 is correspondingly curved on its side of said path of movement that emits the light and faces the path of movement of the containers 4.

Still another feature or aspect of an embodiment is believed at the time of the filing of this patent application to possibly reside broadly in the detection system, wherein the illuminating device 9 or the light source that forms said device are curved such that they are at a constant or substantially constant spacing from the path of movement of the containers 4 over the entire length or at least over a large part of their length.

A further feature or aspect of an embodiment is believed at the time of the filing of this patent application to possibly reside broadly in the detection system, wherein the at least one camera arrangement 8 and the at least one illuminating device 9 that is associated with said camera arrangement are positioned on the side of the path of movement of the containers 4 that is remote from the machine axis (VA).

Another feature or aspect of an embodiment is believed at the time of the filing of this patent application to possibly reside broadly in the detection system, wherein the at least one illuminating device 9 has a constant or substantially constant luminosity on its side that emits light.

Yet another feature or aspect of an embodiment is believed at the time of the filing of this patent application to possibly reside broadly in the detection system, wherein the illuminating device 9 is formed by a plurality of electrically operated elements that emit light, for example LEDs 13.

Still another feature or aspect of an embodiment is believed at the time of the filing of this patent application to possibly reside broadly in the detection system, wherein the at least one camera arrangement 8 has at least two cameras 10 that are located one after the other in the direction of movement A of the conveyor 1.

One feature or aspect of an embodiment is believed at the time of the filing of this patent application to possibly reside broadly in a bottle filling plant comprising a detection apparatus configured to detect at least one profile feature or shape feature such as a label, a banderole, a foil, a foil wrapped around a top neck of a bottle or other container, an enamel label, a plastic seal, a wax seal, or other seal, and a profile feature such as an outlining feature, on containers such as bottles, jars or similar containers, said detection apparatus comprising: a rotary conveying apparatus configured to convey containers to detect at least one shape or feature of containers; at least one illuminating device configured as a curved strip-shaped light source having a length extending in the direction of rotation of containers being conveyed and a width perpendicular to said length; said length being substantially greater than said width, said at least one illuminating device being configured and disposed to simultaneously and steadily illuminate conveyed containers about a substantial portion of rotation of said rotary conveying apparatus, in at least the region of the at least one profile feature or shape feature being detected; said length being sufficient to evenly illuminate several containers disposed on said rotary conveying apparatus; at least one electronic camera disposed to receive light from containers being conveyed; said at least one illuminating device and said at least one electronic camera being disposed outside of a circumference of said rotary conveying apparatus; said at least one illuminating device being adjustable and configured to be disposed at least one of above and below said at least one electronic camera; said detection apparatus further comprising at least one of a) and b): a) said at least one illuminating device being adjustable relative to containers being conveyed and also relative to said at least one electronic camera; said at least one illuminating device being configured to provide different angles of incidence of light, emitted by said at least one illuminating device, onto conveyed containers; and b) said at least one camera being adjustable relative to containers being conveyed and also relative to said at least one illuminating device; said at least one camera being configured to provide different angles for receiving light from conveyed containers; and at least one system for image processing and also adjusting containers, said at least one system for image processing being configured to: compare stored images with images taken by said at least one camera, detect at least one profile feature or shape feature such as a label, a banderole, a foil, a foil wrapped around a top neck of a bottle or other container, an enamel label, a plastic seal, a wax seal, or other seal, and a profile feature such as an outlining feature, on the conveyed containers, and align conveyed containers on said rotary conveying apparatus for further processing.

Another feature or aspect of an embodiment is believed at the time of the filing of this patent application to possibly reside broadly in a bottle filling plant comprising a detection apparatus, wherein said at least one camera is adjustable between a position below said at least one illuminating device and a position above said at least one illuminating device.

Yet another feature or aspect of an embodiment is believed at the time of the filing of this patent application to possibly reside broadly in a bottle filling plant comprising a detection apparatus, wherein at least one of said at least one camera and said at least one illuminating device is adjustable between a position below a path of movement of the at least one profile feature or shape feature of conveyed containers and a position below a path of movement of the at least one profile feature or shape feature of conveyed containers.

Still another feature or aspect of an embodiment is believed at the time of the filing of this patent application to possibly reside broadly in a bottle filling plant comprising a detection apparatus further comprising at least one of a), b) and c): a) said rotary conveying apparatus and said curved strip-shaped light source are configured and disposed to provide substantially constant spacing between containers being detected and said at least one illuminating device, for at least a portion of rotation of said rotary conveying apparatus; b) said at least one illuminating device is configured to substantially constantly emit light at a substantially constant intensity; and c) said at least one camera comprises at least two cameras, disposed one after the other in the direction of rotation of said rotary conveying device.

A further feature or aspect of an embodiment is believed at the time of the filing of this patent application to possibly reside broadly in a bottle filling plant comprising a detection apparatus, wherein said at least one illuminating device comprises one of a) and b): a) a plurality of LEDs configured to provide substantially evenly emitted light throughout said width and said length of said strip-shaped light source; and b) a reflective surface configured to reflect light substantially evenly throughout said width and said length of said strip-shaped light source; and a light source configured to emit light to said reflective surface of said at least one illuminating device.

Another feature or aspect of an embodiment is believed at the time of the filing of this patent application to possibly reside broadly in a detection device configured to detect at least one profile feature or shape feature such as a label, a banderole, a defect, a crack, a scratch, a chip, a bubble, a surface deformation, a foil, a foil wrapped around a top neck of a bottle or other container, an enamel label, a plastic a seal, a wax seal, or other seal, and a profile feature such as an outlining feature, of containers such as bottles, jars or similar containers, said detection device comprising: at least one illuminating device configured as a strip-shaped light source having a length extending in the direction of conveyance of the containers being conveyed and a width transverse to said length; said length being substantially greater than said width; said at least one illuminating device being configured and disposed to illuminate conveyed containers in at least the region of the at least one profile feature or shape feature being detected; at least one electronic camera configured and disposed to receive light from containers being conveyed; and at least one of a) and b) a) said at least one illuminating device being adjustable relative to containers being conveyed and also relative to said at least one electronic camera; said at least one illuminating device being configured to provide different angles of incidence of light, emitted by said at least one illuminating device, onto conveyed containers; and b) said at least one camera being adjustable relative to containers being conveyed and also relative to said at least one illuminating device; said at least one camera being configured to provide different angles for receiving light from conveyed containers; and at least one system for image processing, said at least one system for image processing being configured to compare stored images with images taken by said at least one camera; and said at least one system for image processing being configured to detect at least one profile feature or shape feature of conveyed containers.

Yet another feature or aspect of an embodiment is believed at the time of the filing of this patent application to possibly reside broadly in a detection device, wherein said at least one illuminating device and said at least one camera are disposed on a common side of a conveying apparatus configured to convey containers.

Still another feature or aspect of an embodiment is believed at the time of the filing of this patent application to possibly reside broadly in a detection device, wherein said at least one illuminating device is adjustable between a position below said at least one camera and a position above said at least one camera.

A further feature or aspect of an embodiment is believed at the time of the filing of this patent application to possibly reside broadly in detection device, wherein said at least one camera is adjustable between a position below said at least one illuminating device and a position above said at least one illuminating device.

Another feature or aspect of an embodiment is believed at the time of the filing of this patent application to possibly reside broadly in a detection device, wherein at least one of said at least one camera and said at least one illuminating device is adjustable between a position below a path of movement of the at least one profile feature or shape feature of conveyed containers and a position below a path of movement of the at least one profile feature or shape feature of conveyed containers.

Yet another feature or aspect of an embodiment is believed at the time of the filing of this patent application to possibly reside broadly in a detection device comprising a rotary conveying apparatus configured to convey containers and said at least one illuminating device is configured as a curved strip-shaped light source having its length extending in the direction of rotation of containers being conveyed.

One feature or aspect of an embodiment is believed at the time of the filing of this patent application to possibly reside broadly in a detection device, wherein said rotary conveying apparatus and said curved strip-shaped light source are configured and disposed to provide substantially constant spacing between containers being detected and said at least one illuminating device, for at least a portion of rotation of said rotary conveying apparatus.

Another feature or aspect of an embodiment is believed at the time of the filing of this patent application to possibly reside broadly in a detection device, wherein said at least one illuminating device and said at least one camera are disposed outside of a periphery of said rotary conveying apparatus.

Yet another feature or aspect of an embodiment is believed at the time of the filing of this patent application to possibly reside broadly in a detection device, wherein said at least one illuminating device is configured to substantially constantly emit light at a substantially constant intensity.

Still another feature or aspect of an embodiment is believed at the time of the filing of this patent application to possibly reside broadly in a detection device, wherein said at least one camera comprises at least two cameras, disposed one after the other in the direction of rotation of said rotary conveying device.

A further feature or aspect of an embodiment is believed at the time of the filing of this patent application to possibly reside broadly in a detection device, wherein said at least one illuminating device comprises one of a) and b): a) a plurality of LEDs configured to provide substantially evenly emitted light throughout said width and said length of said strip-shaped light source; and b) a reflective surface configured to reflect light substantially evenly throughout said width and said length of said strip-shaped light source; and a light source configured to emit light to said reflective surface of said at least one illuminating device.

Another feature or aspect of an embodiment is believed at the time of the filing of this patent application to possibly reside broadly in a method of detecting at least one profile feature or shape feature such as a label, a banderole, a defect, a crack, a scratch, a chip, a bubble, a surface deformation, a foil, a foil wrapped around a top neck of a bottle or other container, an enamel label, a plastic a seal, a wax seal, or other seal, and a profile feature such as an outlining feature, of containers such as bottles, jars or similar containers, with a detection device, said detection device comprising: at least one illuminating device configured as a strip-shaped light source having a length extending in the direction of conveyance of the containers being conveyed and a width transverse to said length; said length being substantially greater than said width; said at least one illuminating device being configured and disposed to illuminate conveyed containers in at least the region of the at least one profile feature or shape feature being detected; at least one electronic camera configured and disposed to receive light from containers being conveyed; and at least one of a) and b) a) said at least one illuminating device being adjustable relative to containers being conveyed and also relative to said at least one electronic camera; said at least one illuminating device being configured to provide different angles of incidence of light, emitted by said at least one illuminating device, onto conveyed containers; and b) said at least one camera being adjustable relative to containers being conveyed and also relative to said at least one illuminating device; said at least one camera being configured to provide different angles for receiving light from conveyed containers; and at least one system for image processing, said at least one system for image processing being configured to compare stored images with images taken by said at least one camera; and said at least one system for image processing being configured to detect at least one profile feature or shape feature of conveyed containers, said method comprising the steps of: conveying containers to said detection device; illuminating at least one container along said length of said at least one illuminating device; receiving light with said at least one electronic camera from containers being conveyed; and at least one of a) and b): a) adjusting said at least one illuminating relative to containers being conveyed and also relative to said at least one electronic camera; providing different angles of incidence of light, emitted by said at least one illuminating device, onto conveyed containers; and b) adjusting said at least one camera relative to containers being conveyed and also relative to said at least one illuminating device; providing different angles for receiving light from conveyed containers; rotating the at least one container illuminated with said illuminating device to illuminate the at least one shape or feature being detected and simultaneously expose the at least one shape or feature being detected to said at least one camera; receiving an image of the at least one shape or feature being detected with said at least one camera; processing the light received by said at least one camera with said at least one system for image processing by comparing received images with stored images until the at least one shape or feature on the conveyed containers is detected.

Yet another feature or aspect of an embodiment is believed at the time of the filing of this patent application to possibly reside broadly in method of detecting at least one profile feature or shape feature wherein said detection device further comprises at least one of a), b), c), d) and e): a) said at least one illuminating device and said at least one camera are disposed on a common side of a conveying apparatus configured to convey containers; b) said at least one illuminating device is adjustable between a position below said at least one camera and a position above said at least one camera; c) said at least one camera is adjustable between a position below said at least one illuminating device and a position above said at least one illuminating device; d) at least one of said at least one camera and said at least one illuminating device is adjustable between a position below a path of movement of the at least one profile feature or shape feature of conveyed containers and a position below a path of movement of the at least one profile feature or shape feature of conveyed containers; and e) said at least one camera comprises at least two cameras, disposed one after the other in the direction of movement of conveyed containers.

Still another feature or aspect of an embodiment is believed at the time of the filing of this patent application to possibly reside broadly in a method of detecting at least one profile feature or shape feature wherein said detection device further comprises one of a), b), c), and d): a) a rotary conveying apparatus configured to convey containers; b) a rotary conveying apparatus configured to convey containers; and said at least one illuminating device is configured as a curved strip-shaped light source having its length extending in the direction of rotation of containers being conveyed; c) a rotary conveying apparatus configured to convey containers; said at least one illuminating device is configured as a curved strip-shaped light source having its length extending in the direction of rotation of containers being conveyed; and said rotary conveying apparatus and said curved strip-shaped light source are configured and disposed to provide substantially constant spacing between containers being detected and said at least one illuminating device, for at least a portion of rotation of said rotary conveying apparatus; d) a rotary conveying apparatus configured to convey containers; said at least one illuminating device is configured as a curved strip-shaped light source having its length extending in the direction of rotation of containers being conveyed; said rotary conveying apparatus and said curved strip-shaped light source are configured and disposed to provide substantially constant spacing between containers being detected and said at least one illuminating device, for at least a portion of rotation of said rotary conveying apparatus; said at least one illuminating device and said at least one camera are disposed outside of a periphery of said rotary conveying apparatus; and said at least one illuminating device is configured to substantially constantly emit light at a substantially constant intensity.

A further feature or aspect of an embodiment is believed at the time of the filing of this patent application to possibly reside broadly in a method of detecting at least one profile feature or shape feature, wherein said at least one illuminating device comprises one of a) and b): a) a plurality of LEDs configured to provide substantially evenly emitted light throughout said width and said length of said strip-shaped light source; and b) a reflective surface configured to reflect light substantially evenly throughout said width and said length of said strip-shaped light source; and a light source configured to emit light to said reflective surface of said at least one illuminating device.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

All of the patents, patent applications or patent publications, which were cited in the Federal Republic of Germany dated Dec. 8, 2008, and/or cited elsewhere are hereby incorporated by reference as if set forth in their entirety herein as follows: EP 1 617 208 A1 having the following title "Device for detecting defects of a transparent or translucent object", published on Jan. 18, 2006-01-18; DE 10 2005 023 534 A1, "Device for inspecting labelled containers", published on Nov. 11, 2006; DE 25 16 138 C3, "VERFAHREN UND VORRICHTUNG ZUR PRUEFUNG VON BEHAELTERN AUS GLAS ODER DURCHSICHTIGEM KUNSTSTOFF" published on Oct. 14, 1976; DE 102 57 749 A1, "DEVICE FOR INSPECTING FILLED AND CLOSED RECEPTACLES" published on 2004 Jul. 8; U.S. Pat. No. 6,172,355 B1, "In-line inspection of containers", published on Jan. 9, 2001; U.S. Pat. No. 5,405,015 A, "System and method for seeking and presenting an area for reading with a vision system", published on Apr. 11, 1995; and U.S. Pat. No. 4,509,081, "Optical system for automatic sorting and inspection equipment", published on Apr. 2, 1985.

All of the patents, patent applications or patent publications, which were cited in the International Search Report dated Oct. 5, 2009, and/or cited elsewhere are hereby incorporated by reference as if set forth in their entirety herein as follows: WO 01/55705 A, having the following title "INSTALLATION AND METHOD FOR DETECTING LIGHT REFLECTING FAULTS", published on Aug. 2, 2001; EP 0 222 959 A, "Method of detection of faults, especially cracks, in transparent bodies by optical means"; and DE 102 57 749 A1, "DEVICE FOR INSPECTING FILLED AND CLOSED RECEPTACLES", published on Jul. 8, 2004.

The patents, patent applications, and patent publications listed above in the preceding 2 paragraphs are herein incorporated by reference as if set forth in their entirety. The purpose of incorporating U.S. patents, Foreign patents, publications, etc. is solely to provide additional information relating to technical features of one or more embodiments, which information may not be completely disclosed in the wording in the pages of this application. However, words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, and patent publications, are not considered to be incorporated by reference herein.

The corresponding foreign and international patent publication applications, namely, Federal Republic of Germany Patent Application No. 10 2007 025 524.3, filed on May 31, 2007, having inventors Frank Joachim GROTE and Carsten BUCHWALD, and DE-OS 10 2007 025 524.3 and DE-PS10 2007 025 524.3, and International Application No. PCT/EP2008/004212, filed on May 28, 2009, having WIPO Publication No. WO2008/145346 A1 and inventors Frank Joachim GROTE and Carsten BUCHWALD, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

The purpose of incorporating the corresponding foreign equivalent patent applications, that is, PCT/EP2008/004212 and Federal Republic of Germany Patent Application No. 10 2007 025 524.3, is solely for the purpose of providing a basis of correction of any wording in the pages of the present application, which may have been mistranslated or misinterpreted by the translator. However, words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned word in this sentence, when not used to describe technical features of one or more embodiments of the patents, patent applications, and patent publications, are not generally considered to be incorporated by reference herein.

Statements made in the original foreign patent applications PCT/EP2008/004212 and Federal Republic of Germany Patent Application No. 10 2007 025 524.3 from which this patent application claims priority which do not have to do with the correction of the translation in this patent application are not to be included in this patent application in the incorporation by reference.

Any statements about admissions of prior art in the original foreign patent applications PCT/EP2008/004212 and Federal Republic of Germany Patent Application No. 10 2007 025 524.3 are not to be included in this patent application in the incorporation by reference, since the laws relating to prior art in non-U.S. Patent Offices and courts may be substantially different from the Patent Laws of the United States.

Some examples of bottling systems, which may be used or adapted for use in at least one possible embodiment of the present may be found in the following U.S. patents assigned to the Assignee herein, namely: U.S. Pat. Nos. 4,911,285; 4,944,830; 4,950,350; 4,976,803; 4,981,547; 5,004,518; 5,017,261; 5,062,917; 5,062,918; 5,075,123; 5,078,826; 5,087,317; 5,110,402; 5,129,984; 5,167,755; 5,174,851; 5,185,053; 5,217,538; 5,227,005; 5,413,153; 5,558,138; 5,634,500; 5,713,403; 6,276,113; 6,213,169; 6,189,578; 6,192,946; 6,374,575; 6,365,054; 6,619,016; 6,474,368; 6,494,238; 6,470,922; and 6,463,964.

Some examples of optical scanners which may possibly be utilized or adapted for use in at least one possible embodiment may possibly be found in the following: U.S. Pat. No. 6,719,204, entitled "Mathieu-Gaussian beam for optical scanners;" U.S. Pat. No. 6,603,108, entitled "Image sensing modules for portable optical scanners;" U.S. Pat. No. 6,209,788, entitled "Optical scanners;", and U.S. Pat. No. 6,164,540, entitled "Optical scanners."

Some examples of cameras or the like optical monitoring apparatus that may possibly be utilized or possibly adapted for use in at least one possible embodiment of the present application may possibly be found in the following: U.S. Pat. No. 5,233,186 issued to Ringlien on Aug. 3, 1993; U.S. Pat. No. 5,243,400 issued to Ringlien on Sep. 7, 1993; U.S. Pat. No. 5,369,713 issued to Schwartz et al. on Nov. 29, 1994; U.S. Pat. No. 5,442,446 issued to Gerber et al. on Aug. 15, 1995; U.S. Pat. No. 5,661,295 issued to Buchmann et al. on Aug. 26, 1997; and U.S. Pat. No. 5,898,169 issued to Nodbryhn on Apr. 27, 1999.

Some examples of optical fiber wave guides which may possibly be utilized or adapted for use in at least one possible embodiment may possibly be found in the following: U.S. Pat. No. 6,953,457, entitled "Phototherapeutic wave guide apparatus;" U.S. Pat. No. 6,423,055, entitled "Phototherapeutic wave guide apparatus;" and U.S. Pat. No. 6,294,775, entitled "Miniature image acquisition system using a scanning resonant waveguide."

Some examples of labeling machines which may possibly be utilized in at least one possible embodiment may possibly be found in the following: U.S. Pat. No. 6,634,400, entitled "Labeling machine;" U.S. Pat. No. 6,561,246, entitled "Labeling machine capable of precise attachment of a label to different sizes of containers;" U.S. Pat. No. 6,550,512, entitled "Labeling machine capable of preventing erroneous attachment of labels on containers;" U.S. Pat. No. 6,543,514, entitled "In-line continuous feed sleeve labeling machine and method;" U.S. Pat. No. 6,378,587, entitled "Cylindrical container labeling machine;" U.S. Pat. No. 6,328,086, entitled "Labeling machine;" U.S. Pat. No. 6,315,021, entitled "Labeling machine;" U.S. Pat. No. 6,263,940, entitled "In-line continuous feed sleeve labeling machine and method;" U.S. Pat. No. 6,199,614, entitled "High speed labeling machine having a constant tension driving system;" U.S. Pat. No. 6,167,935, entitled "Labeling machine; U.S. Pat. No. 6,066,223, entitled "Labeling machine and method; U.S. Pat. No. 6,050,319, entitled "Non-round container labeling machine and method;" and U.S. Pat. No. 6,045,616, entitled "Adhesive station and labeling machine."

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

AT LEAST PARTIAL NOMENCLATURE

1 Turntable
2 Rotary disc
3 Setting drive for rotary disc
4 Bottle or container
4.1 Profile feature and/or shape feature
5 Ram
6 Label
7 Optoelectric detection system
8 Camera arrangement
9 Illuminating device
10 Camera
11, 12 Housing
13 LED
14 LED segment
15 Image processing device
16, 17 Additional cameras
A Direction of rotation of the turntable 1
B Adjustment of the cameras 10 or of the camera arrangement 8
C Adjustment of the illuminating device 9
VA Vertical machine axis
DA Rotary disc axis

What is claimed is:

1. An optoelectric detection system, for detecting profile features and/or shape features of containers comprising bottles or similar containers, said optoelectric detection system comprising:

an illumination arrangement comprising a strip-shaped light source disposed to extend along a path of movement of containers to be detected;

said light source being positioned to illuminate an exterior surface region of at least one profile feature and/or shape feature of a container being moved past said light source;

an electronic image detection arrangement comprising an electronic camera being positioned to receive light, emitted from said light source and then reflected off the exterior surface region of the container, to permit detection of the presence and/or location of the at least one profile feature and/or shape feature in the exterior surface region of the container; and one of (A), (B), and (C):

(A) said light source being adjustable to permit movement of said light source in a vertical direction from a vertical position lower than said camera to a vertical position higher than said camera, and vice versa, to produce different angles of incidence of light emitted by said light source;

(B) said camera being adjustable to permit movement of said camera in a vertical direction from a vertical position lower than said light source to a vertical position higher than said light source, and vice versa, to produce different angles of image recording by said camera;

(C) both said camera and said light source being adjustable to permit both:

movement of said light source in a vertical direction from a vertical position lower than said camera to a vertical position higher than said camera, and vice versa, to produce different angles of incidence of light emitted by said light source; and movement of said camera in a vertical direction from a vertical position lower than said light source to a vertical position higher than said light source, and vice versa, to produce different angles of image recording by said camera.

2. The optoelectric detection system according to claim 1, wherein said electronic camera arrangement and said illuminating arrangement are disposed on the same side of the path of movement of containers.

3. The optoelectric detection system according to claim 2, wherein at least one of said light source and said camera is adjustable to permit positioning, in a vertical direction, below a path of movement of the surface features of containers, and above the path of movement of the surface features of containers.

4. The optoelectric detection system according to claim 3, in combination with a rotary carousel configured to rotate about a vertical machine axis to move containers, wherein:

said light source comprises an illuminating side disposed to face toward containers to direct light toward the containers, and a non-illuminating disposed to face away from said containers; and said illuminating side is curved to substantially match the outer curvature of said rotary carousel to direct light toward containers being moved by said rotary carousel.

5. The optoelectric detection system according to claim 4, wherein said illuminating side is curved so as to be at a constant or substantially constant spacing from the path of movement of containers over the entire length or substantially the entire length of said illuminating side.

6. The optoelectric detection system according to claim 5, wherein said electronic camera and said light source are positioned outside of the path of movement of containers and are not connected to said rotary carousel.

7. The optoelectric detection system according to claim 6, wherein said illuminating side has a constant luminosity over its entire length.

8. The optoelectric detection system according to claim 7, wherein said light source comprises a plurality of light emitting elements or LEDs.

9. The optoelectric detection system according to claim 8, wherein said electronic image detection arrangement comprises at least two electronic cameras disposed one after another along a path of movement of containers on said rotary carousel.

10. The optoelectric detection system according to claim 1, wherein said electronic camera is oriented to detect the presence and/or the location of the at least one profile feature and/or the shape feature of the exterior surface region of the container, which the at least one profile feature and/or the shape feature is a raised or recessed integral portion of the body of the container, or a structure attached to the body of the container, that is present upon completion of manufacture of the container prior to labeling.

11. The optoelectric detection system according to claim 10, wherein the at least one profile feature and/or the shape feature comprises a seal, an embossing, or a decoration.

12. The optoelectric detection system according to claim 1, wherein said electronic camera and said light source are oriented such that the light, received by said electronic camera, is reflected off of the exterior surface region of the container directly to said electronic camera without passing through the container.

13. The optoelectric detection system according to claim 1, wherein said electronic image detection arrangement is configured to evaluate an image detected by said electronic camera to determine, based on the detected location of the at least one profile feature and/or shape feature, if the container is in a desired orientation to permit attachment of at least one additional profile feature, comprising a structure to be attached to the body of the container, in a desired position on the container with respect to the at least one profile feature and/or shape feature.

14. A method for detecting profile features and/or shape features of containers comprising bottles or similar containers, said method comprising the steps of:

moving containers along a path of movement past an illuminating arrangement comprising a strip-shaped light source disposed to extend along the path of movement;

illuminating an exterior surface region of at least one profile feature and/or shape feature of a container being moved past said light source;

receiving light, using an electronic camera of an electronic image detection arrangement, emitted from said light source and then reflected off the exterior surface region of the container, and detecting the presence and/or location of the at least one profile feature and/or shape feature in the exterior surface region of the container; and at least one of (A) and (B):

(A) moving said light source in a vertical direction from a vertical position lower than said camera to a vertical position higher than said camera, or vice versa, to produce different angles of incidence of light emitted by said light source; and (B) moving said camera in a vertical direction from a vertical position lower than said light source to a vertical position higher than said light source, or vice versa, to produce different angles of image recording by said camera.

15. The method according to claim 14, wherein the at least one profile feature and/or the shape feature comprises a raised or recessed integral portion of the body of the container, or a structure attached to the body of the container, that is present upon completion of manufacture of the container.

16. The method according to claim 15, wherein the at least one profile feature and/or the shape feature comprises a seal, an embossing, or a decoration.

17. The method according to claim 14, wherein said method further comprises adjusting at least one of said light source and said camera to permit positioning, in a vertical direction, below a path of movement of the surface features of containers, and above the path of movement of the surface features of containers.

18. The method according to claim 14, wherein said method further comprises:

orienting said electronic camera and said light source such that the light, received by said electronic camera, is reflected off of the exterior surface region of the container directly to said electronic camera without passing through the container; and said step of receiving light comprises receiving light reflected off of the exterior surface region of the container directly to said electronic camera without passing through the container.

19. An optoelectric detection system for performing the method according to claim 14, said optoelectric detection system comprising:
  an illumination arrangement comprising a strip-shaped light source disposed to extend along a path of movement of containers to be detected;
  said light source being positioned to illuminate an exterior surface region of at least one profile feature and/or shape feature of a container being moved past said light source;
  an electronic image detection arrangement comprising an electronic camera being positioned to receive light, emitted from said light source and then reflected off of the exterior surface region of the container, to permit detection of the presence and/or location of the at least one profile feature and/or shape feature in the exterior surface region of the container; and
  at least one of said light source and said camera being adjustable to permit said light source to be positioned higher or lower than said camera in a vertical direction, and said camera to be positioned higher or lower than said light source in a vertical direction, to produce different angles of incidence of light emitted by said light source and/or different angles of image recording by said camera.

20. The method according to claim 14, wherein said method further comprises evaluating, using said electronic image detection arrangement, an image detected by said electronic camera, and determining, based on the detected location of the at least one profile feature and/or shape feature, if the container is in a desired orientation to permit attachment of at least one additional profile feature, comprising a structure to be attached to the body of the container, in a desired position on the container with respect to the at least one profile feature and/or shape feature.

* * * * *